(12) United States Patent
Oshige et al.

(10) Patent No.: US 11,267,840 B1
(45) Date of Patent: Mar. 8, 2022

(54) COMPOUND OR SALT THEREOF

(71) Applicants: M.T.3, Inc., Tokyo (JP); NATIONAL UNIVERSITY CORPORATION GUNMA UNIVERSITY, Maebashi (JP)

(72) Inventors: Masahiko Oshige, Isesaki (JP); Ichiro Matsuo, Kiryu (JP); Hiroaki Horiuchi, Kiryu (JP); Shinji Katsura, Kiryu (JP); Fumio Sugawara, Tokyo (JP); Kengo Sakaguchi, Tsukuba (JP)

(73) Assignees: M.T.3, INC., Tokyo (JP); NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 0 days.

(21) Appl. No.: 17/464,810

(22) Filed: Sep. 2, 2021

(30) Foreign Application Priority Data

Sep. 25, 2020 (JP) .............................. JP2020-161281

(51) Int. Cl.
*C07H 15/04* (2006.01)
*C07H 7/02* (2006.01)

(52) U.S. Cl.
CPC ............... *C07H 7/02* (2013.01); *C07H 15/04* (2013.01)

(58) Field of Classification Search
None
See application file for complete search history.

(56) References Cited

U.S. PATENT DOCUMENTS

| 7,973,145 | B2 * | 7/2011 | Ohta | .................. | A61K 41/0038 536/4.1 |
|---|---|---|---|---|---|
| 2002/0028776 | A1 | 3/2002 | Yamazaki et al. | | |
| 2007/0219145 | A1 | 9/2007 | Sakimoto et al. | | |
| 2009/0209475 | A1 | 8/2009 | Ohta et al. | | |
| 2010/0202971 | A1 | 8/2010 | Ohta et al. | | |

FOREIGN PATENT DOCUMENTS

| JP | 3927993 B2 | 6/2007 |
|---|---|---|
| JP | 4435861 B2 | 3/2010 |
| JP | 2016150905 A | 8/2016 |
| WO | 0051622 A1 | 9/2000 |
| WO | 2009014101 A1 | 1/2009 |
| WO | 2010082634 A1 | 7/2010 |
| WO | 2020179125 A1 | 9/2020 |

OTHER PUBLICATIONS

Hall, Eric J., et al., Radiobiology for the Radiologist 2nd Edition, Chapter 9 "Chemical and Pharmacological Modifiers", Nov. 1, 1995, pp. 172-194, Harper & Row Publishers, Hagerstown, Maryland, US, and Shinoharashinsha Publishers, Inc. (40 pages).
Li, Lei, et al., "Functional biomimetic nanoparticles for drug delivery and theranostic applications in cancer treatment", Science and Technology of Advanced Materials, Oct. 26, 2018, pp. 771-790, vol. 19, No. 1, Informa UK Ltd, trading as Taylor & Francis Group. (21 pages).
Notice of Reasons for Refusal with English translation dated Jan. 8, 2021 issued in corresponding Japanese Patent Application No. 2020-161281. (5 pages).
Takahashi, Junko, et al., "Elucidation of the action mechanism of combined treatment with X-ray irradiation and 5-aninolevulinic acid by trantcriptome analysis", [online] Grants-in Aid for Scientific Research, 2017, [Searched on Sep. 10, 2020], Internet <URL:https://kaken.nii.ac.jp/ja/grant/KAKENHI-PROJECT-25293270/>. (6 pages).

* cited by examiner

*Primary Examiner* — Traviss C McIntosh, III
(74) *Attorney, Agent, or Firm* — Buchanan Ingersoll & Rooney PC

(57) ABSTRACT

There is provided with a compound. The compound is represented by formula or a salt thereof. $R_1$ is an aliphatic hydrocarbon group having 10 to 26 carbon atoms.

2 Claims, 15 Drawing Sheets

US 11,267,840 B1

COMPOUND OR SALT THEREOF

CROSS-REFERENCE TO RELATED APPLICATION(S)

This application claims priority to and the benefit of Japanese Patent Application No. 2020-161281 filed on Sep. 25, 2020, the entire disclosure of which is incorporated herein by reference.

BACKGROUND OF THE INVENTION

Field of the Invention

The present invention relates to a compound or a salt thereof.

Description of the Related Art

Half of causes of death of Japanese are three major diseases of malignant tumor, heart disease, and cerebrovascular disease (2017 vital statistics of the Ministry of Health, Labour and Welfare). The malignant tumor is the top cause of death, and the number of deaths due to the malignant tumor is still increasing today. As three major treatment methods for malignant tumors, surgical treatment, chemotherapy, and radiation therapy are known. Radiation therapies such as external irradiation performed using electron beams, X-rays, gamma rays, proton beams, or heavy particle beams and internal irradiation such as brachytherapy are attracting attention from the standpoint of giving importance to quality of life (QOL) of patients.

Halogenated pyrimidine and hypoxic cell sensitizers are known as chemical or pharmaceutical substances that are administered at the same time as radiation in radiation therapy to enhance therapeutic effects of the radiation, that is, as radiosensitizers that can be put into practical clinical use (e.g., see Eric J. Hall et al., translated by Urano Muneyasu, "Radiobiology for the Radiologist", Shinoharashinsha Publishers Inc., Nov. 1, 1995). Also, misonidazole is known as a hypoxic cell sensitizer, for example.

Japanese Patent No. 3927993 discloses, as another radiosensitizer, a radiosensitizer constituted by sulfopyranosylacylglycerol or a salt thereof. Also, Japanese Patent No. 4435861 discloses a radiosensitizer constituted by sulfoquinovosylacyl propanediol or a salt thereof.

SUMMARY OF THE INVENTION

According to one embodiment of the present invention, a compound is represented by the following formula (I) or a salt thereof,

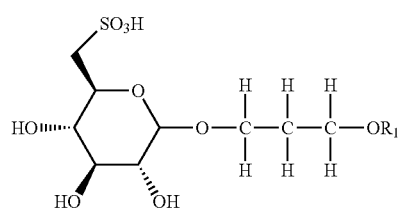

(I)

wherein $R_1$ is an aliphatic hydrocarbon group having 10 to 26 carbon atoms.

According to another embodiment of the present invention, the compound according to claim 1 or a salt thereof, wherein $R_1$ is an octadecyl group.

Further features of the present invention will become apparent from the following description of exemplary embodiments (with reference to the attached drawings).

DESCRIPTION OF THE EMBODIMENTS

Figure 1:
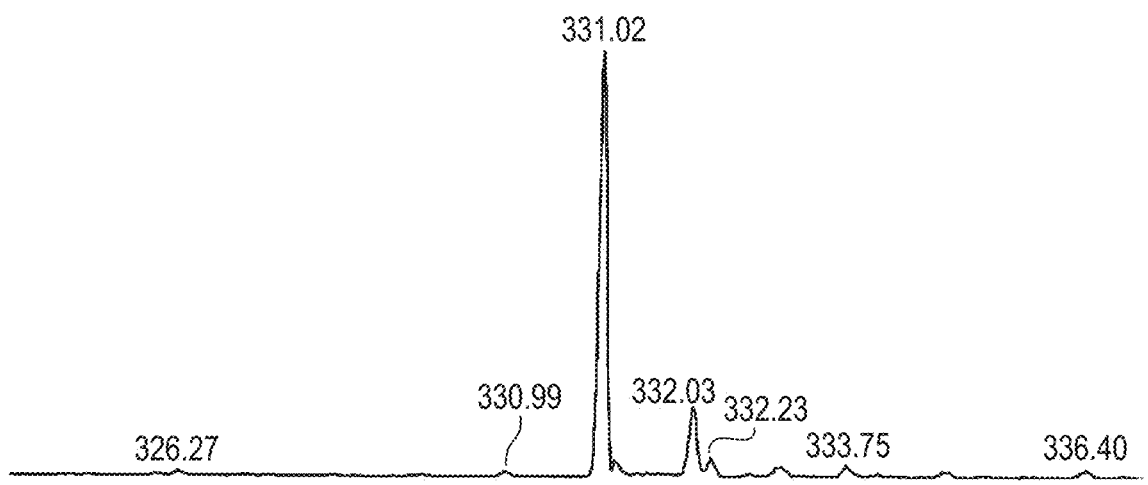
FIG. 1 is a diagram showing a result of mass spectrometry of a compound represented by structural formula (3).

Hereinafter, embodiments will be described in detail with reference to the attached drawings. Note that the following embodiments are not intended to limit the scope of the claimed invention, and limitation is not made an invention that requires all combinations of features described in the embodiments. Two or more of the multiple features described in the embodiments may be combined as appropriate. Furthermore, the same reference numerals are given to the same or similar configurations, and redundant description thereof is omitted.

Radiosensitizers such as those described in "Radiobiology for the Radiologist", Eric J. Hall et al., translated by Urano Muneyasu, Shinoharashinsha Publishers Inc., Nov. 1, 1995 have problems to be solved, such as gastrointestinal injury, peripheral nerve toxicity, or other side effects, and most of the radiosensitizers have not yet been put into practical use. Therefore, a novel pharmaceutical compound that can be used in treatment performed using radiation is desired.

An embodiment of the present invention can provide a novel pharmaceutical compound that can be used in combination with radiation in tumor treatment.

A compound according to an embodiment of the present invention is represented by the following general formula (I).

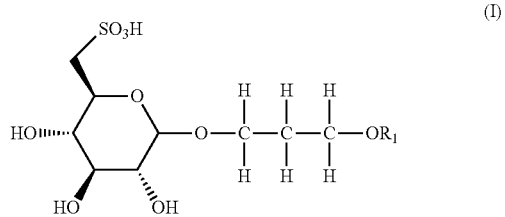

In general formula (I), $R_1$ represents an aliphatic hydrocarbon group. The number of carbon atoms included in $R_1$ is not particularly limited, but may be, for example, 1 or more, 3 or more, 10 or more, 12 or more, 14 or more, or 16 or more. Also, the number of carbon atoms included in $R_1$ may be 26 or less, or 24 or less, and is more preferably 22 or less. Examples of the aliphatic hydrocarbon group include alkyl groups such as a methyl group, a hexyl group, a dodecyl group, an octadecyl group, and icosyl group, alkenyl groups such as a hexenyl group, a dodecenyl group, an octadecenyl group, and an icosenyl group, and alkynyl groups such as a dodecynyl group, an octadecynyl group, and an icosynyl group.

In an embodiment, a quinovose ring included in the compound (3-(n-octadecyloxy)-n-propylsulfoquinovoside derivative) represented by general formula (I) may have a boat shape or a chair shape, or the boat shape and the chair shape may be mixed, but the chair shape is preferable because it generally is more stable. Also, in general formula (I), propanediol (—O—$C_3H_6$—$OR_1$) is bonded to the quinovose ring, and the steric configuration of the propanediol with respect to the quinovose ring may be an α-anomer or a β-anomer, or the α-anomer and the β-anomer may be mixed.

In a synthesis process according to an embodiment, the $R_1$ moiety in general formula (I) is provided using an alcohol compound. The alcohol compound may be a saturated alcohol or an unsaturated alcohol. Also, the alcohol compound may be a straight chain compound or a branched chain compound. Examples of saturated alcohols include 1-hexanol and 1-octadecanol. Examples of unsaturated alcohols include 1-hexen-6-ol and 1-octadecene-18-ol.

A compound according to another embodiment of the present invention is a salt of the compound represented by general formula (I) shown above. For example, a salt of a monovalent positive ion such as sodium or potassium or a salt of a divalent positive ion such as calcium or magnesium may be used as the salt. In the present invention, a sulfo group in formula (I) may form the salt, for example.

Although there is no particular limitation on the method for synthesizing the compound represented by the above general formula (I), for example, the compound is synthesized through pathways A to J shown below. By performing acid treatment on an obtained compound (11), the compound represented by general formula (I) can be obtained. The compound can be manufactured easily because no asymmetric carbon atom is newly generated in the synthesis process shown below. Also, according to the following synthesis process, it is easy to manufacture the compound so as to have high purity.

In a synthesis method described in Patent Document 1, a terminal double bond of an allyl group is hydroxylated to form a glycerol skeleton and position 2 of the glycerol moiety becomes an asymmetric carbon atom, and accordingly, stereoisomers due to an alcohol group are generated approximately at the ratio of 1:1. Such a compound is not suitable to be used as a pharmaceutical product, and in order to selectively synthesize each stereoisomer, a complex procedure is required and this is disadvantageous in terms of cost as well.

Also, in the case of a sulfopyranosylacylglycerol derivative, a structural isomer (2-acyl isomer) is generated in an amount of several % as a result of an acyl group at position 1 of glycerol (1-acyl isomer) transferring to position 2 between molecules and/or in a molecule. Such a stereoisomer or structural isomer is generated even during preservation, and therefore, it is chemically difficult to supply a sulfopyranosylacylglycerol derivative having high purity. On the other hand, in the compound represented by general formula (I) according to an embodiment, a hydroxy group that tends to transfer is not present near the $R_1$ group, and therefore, the compound can be preserved in a structurally stable state.

Here, "Cm:n" indicates that the number of carbon atoms included in the $R_1$ group in general formula (I) is m, and the number of double bonds is n (m is an integer greater than or equal to 1, and n is an integer greater than or equal to 0). Also, "Ph" represents a phenyl group, "Bn" represents a benzyl group, "Ts" represents a tosyl group, and "SAc" represents a thioacetyl group.

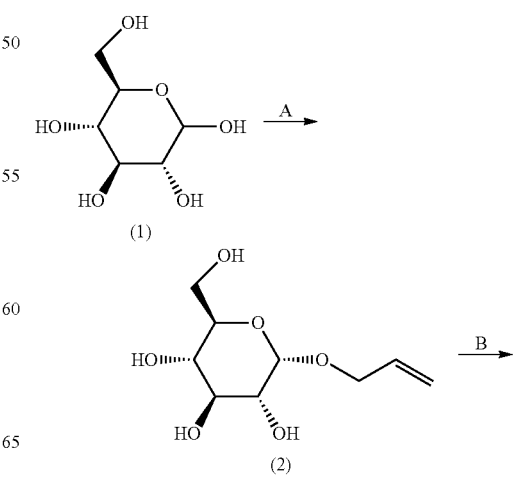

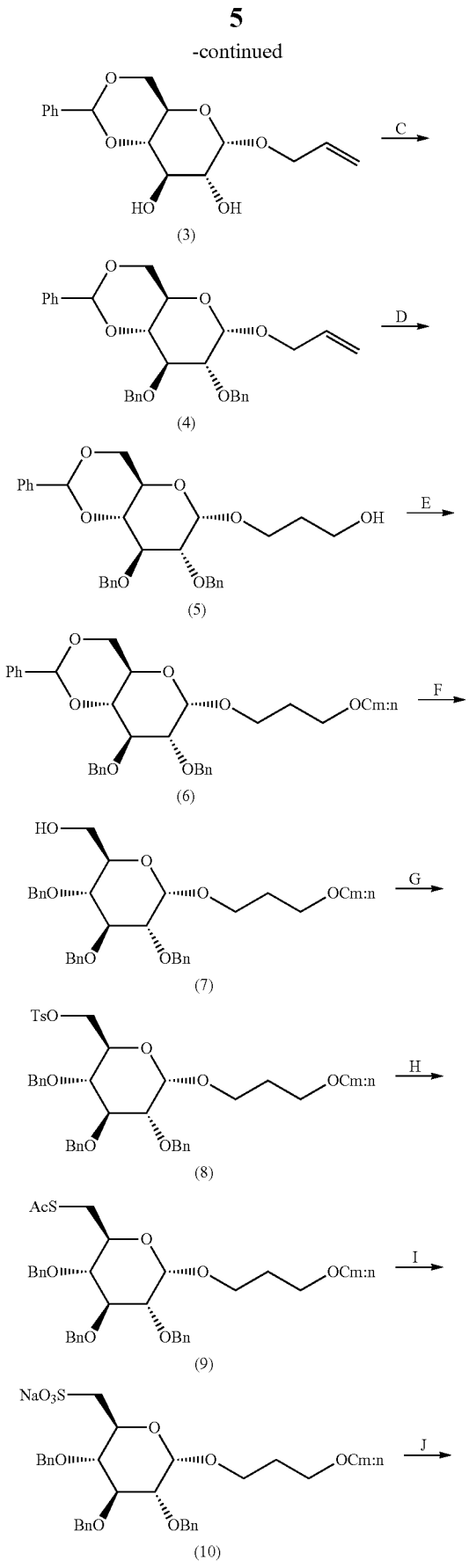

A salt of the compound according to an embodiment of the present invention can be manufactured in this synthesis method or a method obtained by modifying the synthesis method. Also, a salt of the compound according to an embodiment of the present invention can be obtained by performing known ion exchange treatment according to the salt to be obtained, after the synthesis is performed using this method. These methods for synthesizing a salt according to the present invention are also encompassed in the scope of the present invention.

The compound represented by general formula (I) according to the present invention and pharmaceutically acceptable salts thereof can be used for treatment of tumors such as malignant tumors. Examples of malignant tumors include neurogenic tumors including brain tumors and the like, the following cancers classified into cancers such as squamous cell carcinoma and adenocarcinoma (head and neck cancer, skin cancer, esophageal cancer, thyroid cancer, gastric cancer, lung cancer, gallbladder cancer, biliary tract cancer, pancreatic cancer, liver cancer, prostate cancer, uterine cancer, ovarian cancer, breast cancer, renal cancer, bladder cancer, large bowel cancer, etc.), melanoma, bone and soft tissue tumor, lymphoma, leukemia, and myeloma, but there are no limitation thereto. As used herein, "treatment" refers to making a malignant tumor such as those described above small, eliminating the malignant tumor, and suppressing the growth of the malignant tumor, or any of these.

In radiation therapy, reactive oxygen species (ROS) is generated from oxygen, water molecules, and the like through irradiation, and treatment of cancer tissue is performed by causing gene damage and cell damage via the ROS, for example. Here, the irradiation may be external irradiation performed using electron beams, X-rays, gamma rays, proton beams, heavy particle beams, or the like, or internal irradiation such as brachytherapy.

On the other hand, in a tumor microenvironment that surrounds the cancer tissue, excessive cell proliferation occurs in many cases, and a low-oxygen environment is generated as a result of vascularization cannot keep up with the excessive cell proliferation. In addition, a large amount of antioxidant enzyme exists in the tumor microenvironment, and accordingly, even when irradiation is performed, the ROS is unlikely to be generated and most of generated ROS is decomposed by the antioxidant enzyme, and it is difficult to achieve effects of the treatment.

Here, for example, Junko Takahashi et al, "Elucidation of the action mechanism of combined treatment with X-ray irradiation and 5-aninolevulinic acid by trantcriptome analysis," [online] Grants-in Aid for Scientific Research, 2017 [Searched on Sep. 10, 2020], Internet <URL:https://kaken.nii.ac.jp/ja/grant/KAKENHI-PROJECT-25293270/> discloses 5-aminolevulinic acid (ALA) being able to be used as a radiosensitizer in photodynamic therapy. When the ALA is taken into a living body, the ALA causes tumor cells to accumulate PpIX at a high concentration, and the PpIX generates reactive oxygen through photoexcitation, for example. As described above, substances that generate reactive oxygen and cause gene damage are used as radiosensitizers.

The compound represented by general formula (I) according to the present invention and pharmaceutically acceptable salts thereof are accumulated in cancer tissue when administered, and induce generation of the ROS. According to Example, which will be described later, the compound represented by general formula (I) and pharmaceutically acceptable salts thereof induce generation of the ROS in an amount that is equivalent to that generated with use of a known sulfoquinovosylacyl propanediol derivative that is used as a radiosensitizer.

Therefore, the compound represented by general formula (I) according to the present invention and pharmaceutically acceptable salts thereof can be used as an agent for emitting the ROS within a living body. Also, the compound represented by general formula (I) according to the present invention and pharmaceutically acceptable salts thereof can be used as a pharmaceutical compound that is used in combination with radiation in tumor treatment and improves effects of the radiation by inducing generation of the ROS.

According to an aspect of the present invention, the compound represented by general formula (I) and pharmaceutically acceptable salts thereof have a radiosensitizing effect. Therefore, the compound represented by general formula (I) and pharmaceutically acceptable salts thereof may be provided as a radiosensitizer.

A radiosensitizer according to the present invention may contain, as an active ingredient, an effective amount of at least one selected from the group consisting of the above-described compound represented by general formula (I), pharmaceutically acceptable salts thereof, pharmaceutical derivatives that uses pharmacological action of the compound, and pharmaceutically acceptable salts of the derivatives. Furthermore, the compound represented by general formula (I) may be used in combination with another radiosensitizer, an antitumor agent, or either one or both of another pharmacologically active substance and another pharmaceutically active substance, so long as activity of the compound is not adversely affected.

Also, in this case, administration conditions (e.g., dose, the number of doses, dose interval, etc.) of the compound represented by general formula (I) can be set or adjusted as appropriate according to the dosage form, the administration route, the target disease, for example, the state (e.g., type, location, progression stage) of a malignant tumor, conditions regarding a concomitant drug or the like (e.g., the presence or absence of a concomitant drug, type, amount, the number of times, when the drug is used in combination with the compound, in which order the anti-malignant neoplasm agent is administered, etc.), and the state (e.g., weight, sex, age, etc.) of the subject of the treatment.

The compound represented by general formula (I) according to the present invention and pharmaceutically acceptable salts thereof can be administered orally or parenterally, for example. The compound represented by general formula (I) according to the present invention and pharmaceutically acceptable salts thereof can be formed into a pharmaceutical formulation by being combined with pharmaceutical additives such as an appropriate pharmaceutically acceptable excipient and a diluent depending on these administration routes.

Examples of dosage forms that are suitable for oral administration include forms that are in a solid state, a semi-solid state, a liquid state, or a gas state, and more specific examples thereof include tablets, capsules, powders, granules, solutions, suspensions, syrups, elixir, and aerosols, but there is no limitation thereto.

In cases where the compound represented by general formula (I) according to the present invention and pharmaceutically acceptable salts thereof are administered parenterally, the compound and the salts may be administered by injection, percutaneous administration, rectal administration, intraocular administration, and the like.

In the case where administration is performed by injection, the compound and the salts can be administered beneath the skin, within the dermis, within a vein, or within a muscle, for example.

Administration conditions (e.g., dose, the number of doses, dose interval, etc.) of the compound represented by general formula (I) according to the present invention and pharmaceutically acceptable salts thereof can be set or adjusted as appropriate according to the dosage form, the administration route, the target disease, for example, the state (e.g., type, location, progression stage) of a malignant tumor, conditions regarding a concomitant drug or the like (e.g., the presence or absence of a concomitant drug, type, amount, the number of times, when the drug is used in combination, in which order the compound of the present invention is administered, etc.), how the compound is used in combination with radiation (e.g., when the radiosensitizer of the present invention is used in combination with radiation, in which order the radiosensitizer is administered, etc.), and the state (e.g., weight, sex, age, etc.) of the subject of the treatment.

In an example, the compound represented by general formula (I) according to the present invention and pharmaceutically acceptable salts thereof can be administered in an amount of 0.001 to 100 mg/kg weight/day in the case of oral administration, in an amount of 0.001 to 50 mg/kg weight/day in the case of injection, in an amount of 0.001 to 100 mg/kg weight/day in the case of percutaneous administration, in an amount of 0.001 to 50 mg/kg weight/day in the case of rectal administration, and by administering a solution of about 0.001 to 3% several times per day in the case of intraocular administration, but there is no limitation thereto.

On the other hand, in radiation therapy, the type and dose of radiation, and the number of times of irradiation can be set to be similar to those in conventional radiation therapy. In specific examples of conventional irradiation of a human body, irradiation is performed with medical radiation such as X-rays, γ-rays, electron beams, or β-rays, or particle beams of π-mesons, neutrons, or other heavy particles, in amount of about 0.1 to 100 Gy per single dose over a period of 1 week to 6 months such that a total irradiation amount is about 10 to 500 Gy. In a typical example of irradiation of a human body, irradiation is performed five times per week with 2 Gy of X-rays per single dose, for about 6 weeks so that a total irradiation amount is 60 Gy, but there is no limitation thereto. For example, the irradiation amount or the number of times of irradiation can be reduced. Also, irradiation can be performed by conformation radiation therapy, stereotactic radiation therapy in which irradiation is performed by precisely focusing on a focus of a malignant tumor, intensity modulated radiation therapy, or the like. In addition, irradiation can be performed using a small sealed radiation source, remote γ-ray irradiation, or particle rays. Note that in the case of internal irradiation, the irradiation amount per single dose can be increased and the irradiation period can be reduced.

It is possible to perform irradiation and administration of the compound represented by general formula (I) according to the present invention and pharmaceutically acceptable salts thereof at the same time or perform either one of these in advance to the other. In this case, the compound represented by general formula (I) according to the present invention and pharmaceutically acceptable salts thereof are expected to function as an anti-malignant tumor agent used in combination with irradiation. Therefore, the compound represented by general formula (I) according to the present invention and pharmaceutically acceptable salts thereof may be provided as a pharmaceutical compound such as an anti-malignant tumor agent that is used in combination with irradiation.

As is well known in the field of radiation therapy, health care professionals and other professionals can select conditions for the above-described irradiation and conditions for administration of the compound represented by general formula (I) according to the present invention and pharmaceutically acceptable salts thereof as appropriate depending on: the type of radiation source, the irradiation method, the to-be-irradiated portion, the irradiation period; the type of sensitizer, the administration route, when the sensitizer is to be administered; the type and seriousness of the disease to be treated; the age, weight, state of health, and medical history of the subject to be irradiated; and the like.

Another aspect of the present invention provides a treatment method for treating a disease for which irradiation is effective, the method including administering an effective amount of the compound represented by general formula (I) according to the present invention or a pharmaceutically acceptable salt thereof to a target that needs the compound or the salt. Here, the "disease for which irradiation is effective" refers to a disease such as the malignant tumors described above, for which irradiation is effective to treat the disease. Details of the compound represented by general formula (I) according to the present invention and the pharmaceutically acceptable salt thereof, the administration method, administration conditions, and the like may be the same as those described above.

Also, the treatment method according to the present invention may include administering the compound represented by general formula (I) according to the present invention or the pharmaceutically acceptable salt thereof to the target that needs the compound or the salt at the same time as or before or after irradiation.

Commonly, hydrolases such as lipase, protease, or glycosidase increase in cancer cells, as shown in Lei Li et al. "Functional biomimetic nanoparticles for drug delivery and theranostic applications in cancer treatment", Science and Technology of Advanced Materials, 2018 Oct. 26; vol. 19(1): p. 771-790. The compound represented by general formula (I) according to the present invention and pharmaceutically acceptable salts thereof do not have an ester bond, and therefore are stable against lipase, for example. In Example described below, it is shown that the compound represented by general formula (I) according to the present invention and pharmaceutically acceptable salts thereof continuously exhibit effectiveness as a sensitizer in cancer tissue for a longer period of time than a sulfopyranosylacyl propanediol derivative.

EXAMPLE

Example 1

The following describes an example of a method for synthesizing a sodium salt represented by structural formula (11) as an example of general formula (I). In this example, 3-(n-octadecyloxy)-n-propyl-α-D-quinovopyranoside sodium salt (Cm:n in structural formula (11) is an octadecyl group) was synthesized through the pathways A to J described above.

In the pathway A, allyl-α-D-glucopyranoside (structural formula (2)) was synthesized. The atmosphere in a 500 mL eggplant flask was replaced with argon, and allyl alcohol (250 mL) was put into the flask. α-D-glucopyranose (structural formula (1)) (50 g) was added into the flask while contents in the flask were stirred, and camphorsulfonic acid (1.9 g) was added into the flask while the contents in the flask were cooled to 0° C. with ice water. Then the flask was taken out from an ice bath and brought back to the room temperature, heated to 80° C., and the contents in the flask were stirred for 16 hours. Thereafter, the compound represented by structural formula (2) was obtained as a residue after vacuum concentration.

In the pathway B, allyl-4,6-O-benzylidene-α-D-glucopyranoside (structural formula (3)) was synthesized. 100 mL of anhydrous N,N-dimethylformamide and 100 mL of acetonitrile were added to the residue of the pathway A, the resultant mixture was cooled to 0° C. with ice water, and benzaldehyde dimethylacetal (103 mL) and toluenesulfonic acid monohydrate (2.5 g) were added. Then, after the mixture was stirred at 40° C. for 16 hours while being heated, triethylamine (10 mL) was added to stop reaction, and vacuum concentration was performed. The resultant residue was poured into hexane (180 mL) and water (150 mL), and the liquid mixture was stirred vigorously. The resultant precipitate was filtered and washed with cold water and hexane, in this order. The precipitate was further washed with hexane, cold water, and hexane, in this order, was filtered, and crystalized from ethanol to obtain the compound represented by structural formula (3) (28.6 g, 57.2%) as colorless acicular crystals.

Figure 2:
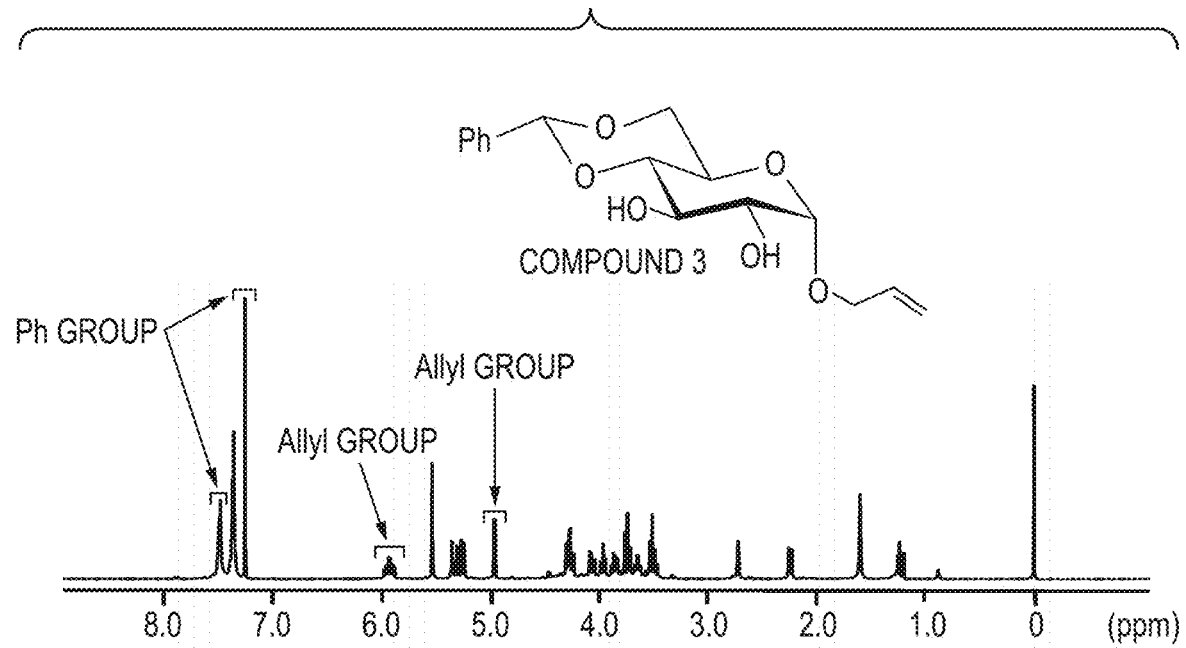
FIG. 2 is a diagram showing a result of $^1$H-NMR measurement of the compound represented by structural formula (3).

Mass spectrometry and a $^1$H-NMR spectrum of the compound represented by structural formula (3) are shown in FIGS. 1 and 2.

In this example, a mass spectrometer (AXIMA MALDI-7090 TOFMS, manufactured by SHIMADZU CORPORATION) was used in the mass spectrometry. Also, the following measurement of $^1$H-NMR spectra was performed using a spectrometer (ECS400 400 MHz, manufactured by JEOL) and CDCl3 as a solvent. Data of the mass spectrometry and the $^1$H-NMR spectrum of the compound represented by structural formula (3) is shown below.

MS: measurement value m/z 331.02 [M+Na], calculation value 308.33 [M]

δ: 7.6-7.2 (5H), 6.0-3.5 (13H)

In the pathway C, allyl-2,3-di-O-benzyl-4,6-O-benzylidene-α-D-glucopyranoside (structural formula (4)) was synthesized. The compound (10.0 mg) represented by structural formula (3) was cooled to 0° C. with ice water, anhydrous N,N-dimethylformamide (181.5 mL) and 60% NaH (3.1 g) were added, and the resultant mixture was stirred at the room temperature for 10 minutes. The mixture was again cooled to 0° C. with ice water, benzyl bromide (9.7 mg) was added, and the mixture was stirred at the room temperature for 1 hour. Next, after the reaction liquid was neutralized by adding triethylamine (11.4 mL) and methanol (11.4 mL), the reaction liquid was poured into cold water (900 mL), and extraction was performed with ethyl acetate (300 mL, three times). After washing was performed with a saturated saline solution, an organic phase was dried using magnesium sulfate and filtered, and a reaction product (17.92 g) was obtained through vacuum concentration. The reaction product was purified using silica gel chromatography (mixed solution of hexane and ethyl acetate) to obtain the compound represented by structural formula (4) (4.9 g, 48.7%).

Figure 3:
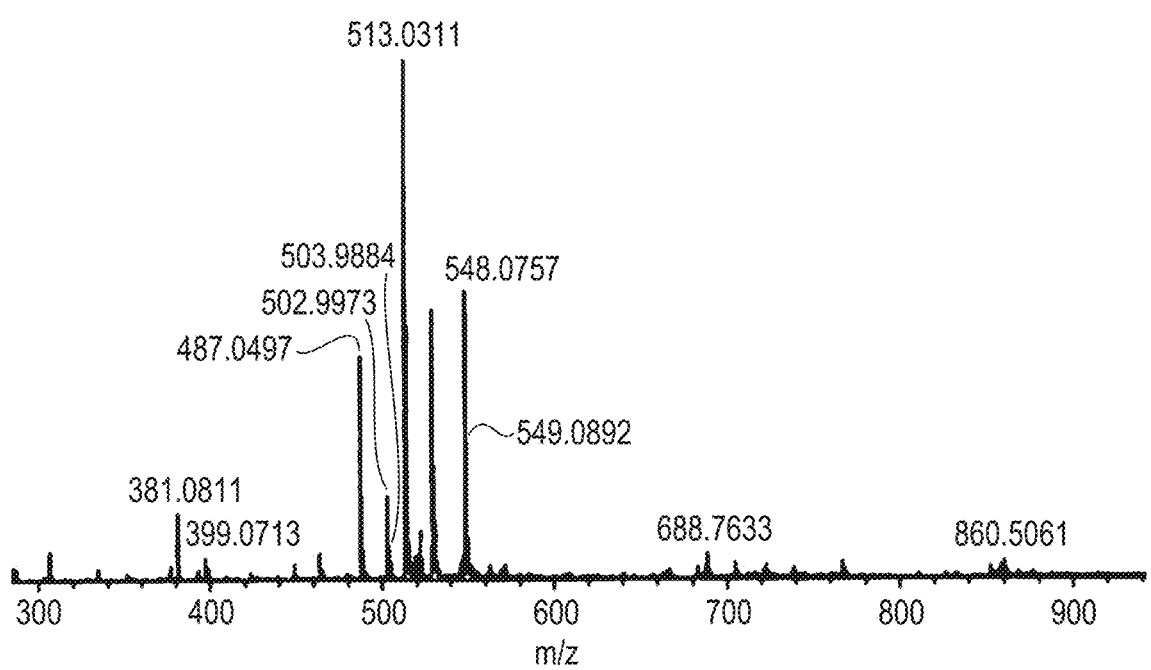
FIG. 3 is a diagram showing a result of mass spectrometry of a compound represented by structural formula (4).
Figure 4:
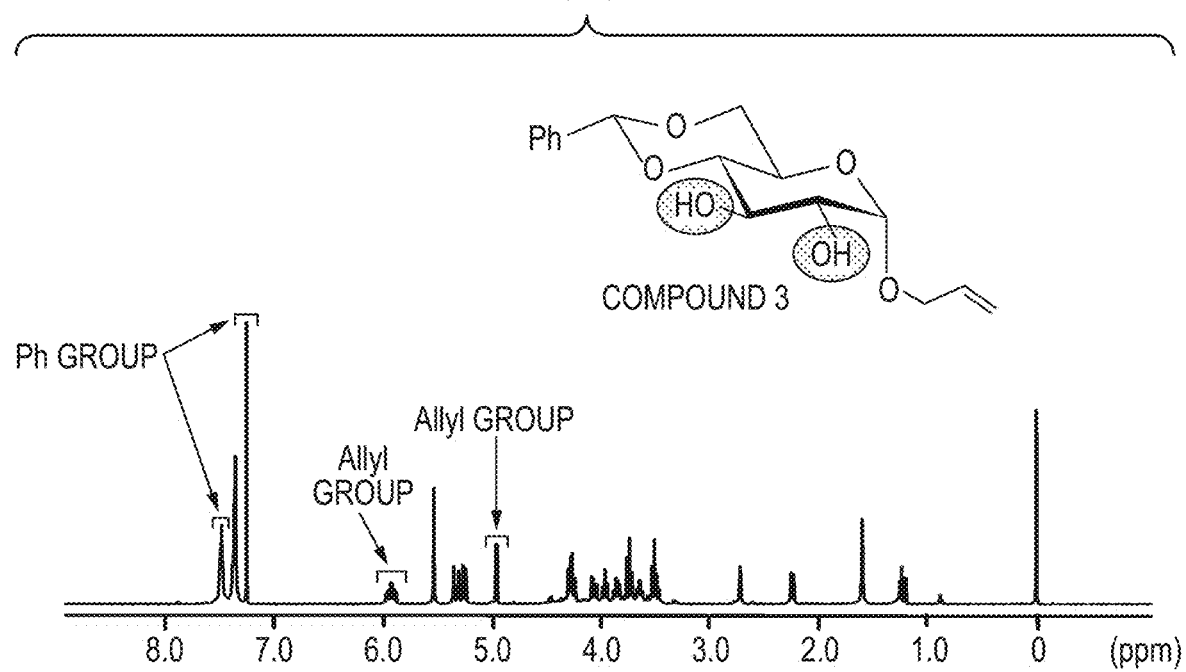
FIG. 4 is a diagram showing a result of $^1$H-NMR measurement of the compound represented by structural formula (4).
Figure 4:
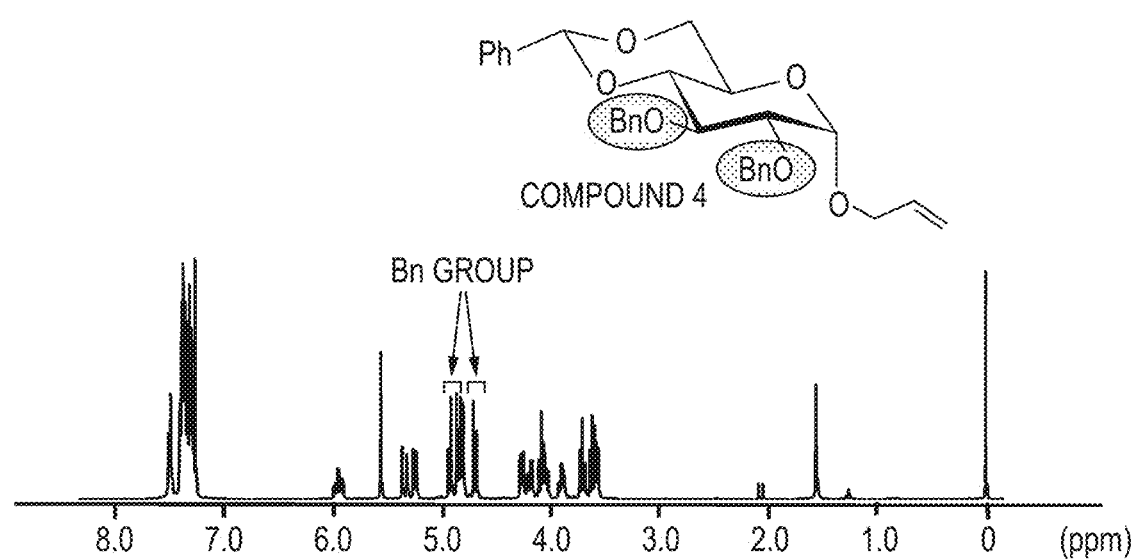

Mass spectrometry and a $^1$H-NMR spectrum of the compound represented by structural formula (4) are shown in FIGS. 3 and 4.

Data of the mass spectrometry and the $^1$H-NMR spectrum of the compound represented by structural formula (4) is shown below.

MS: measurement value m/z 513.03 [M+Na], calculation value 488.58 [M]

δ: 7.6-7.2 (15H), 6.0-3.5 (17H)

In the pathway D, 3-hydroxy-n-propyl-2,3-di-O-benzyl-4,6-O-benzylidene-α-D-glucopyranoside (structural formula (5)) was synthesized. A 0.5 M tetrahydrofuran solution (8.2 mL) of 9-borabicyclo[3,3,1]nonane (9-BBN) was added to an anhydrous tetrahydrofuran solution (150 mL) of the compound (1.0 g) represented by structural formula (4) in an argon atmosphere at 0° C. After 1 hour passed, the reaction liquid was brought back to the room temperature, and was successively stirred for 2 hours. Then, the reaction liquid was again cooled to 0° C., a 3 M sodium hydroxide solution (10 mL) and 30% hydrogen peroxide water (1 mL) were added in order, and after 1 hour passed, the reaction liquid was brought back to the room temperature and stirred for 16 hours. After it was confirmed that reaction had sufficiently progressed, extraction was performed on the solution using ethyl acetate (100 mL, three times), and a collected organic phase was washed with a saturated saline solution (100 mL, two times), and thereafter was dried using sodium sulfate and filtered, and then concentrated in a vacuum. The resultant residue (1.8 g) was dissolved in chloroform and purified using silica gel chromatography (mixed solution of hexane and ethyl acetate) to obtain the compound represented by structural formula (5) (1.0 g, 99.0%) as a colorless oily substance.

Figure 5:
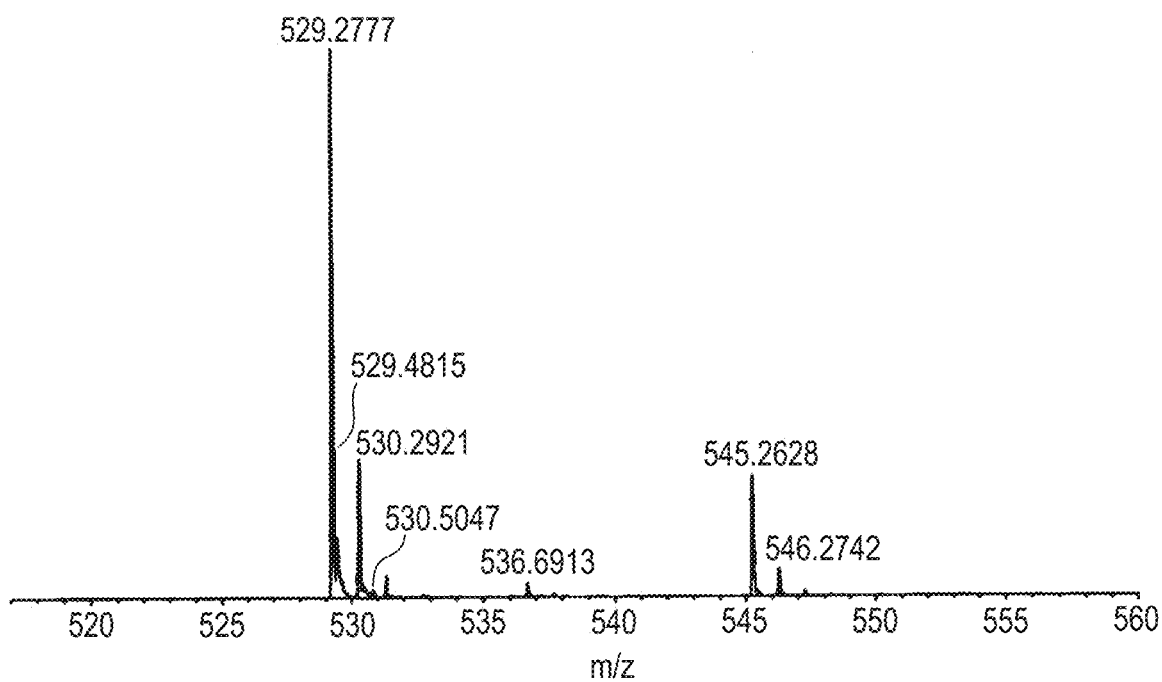
FIG. 5 is a diagram showing a result of mass spectrometry of a compound represented by structural formula (5).
Figure 6:
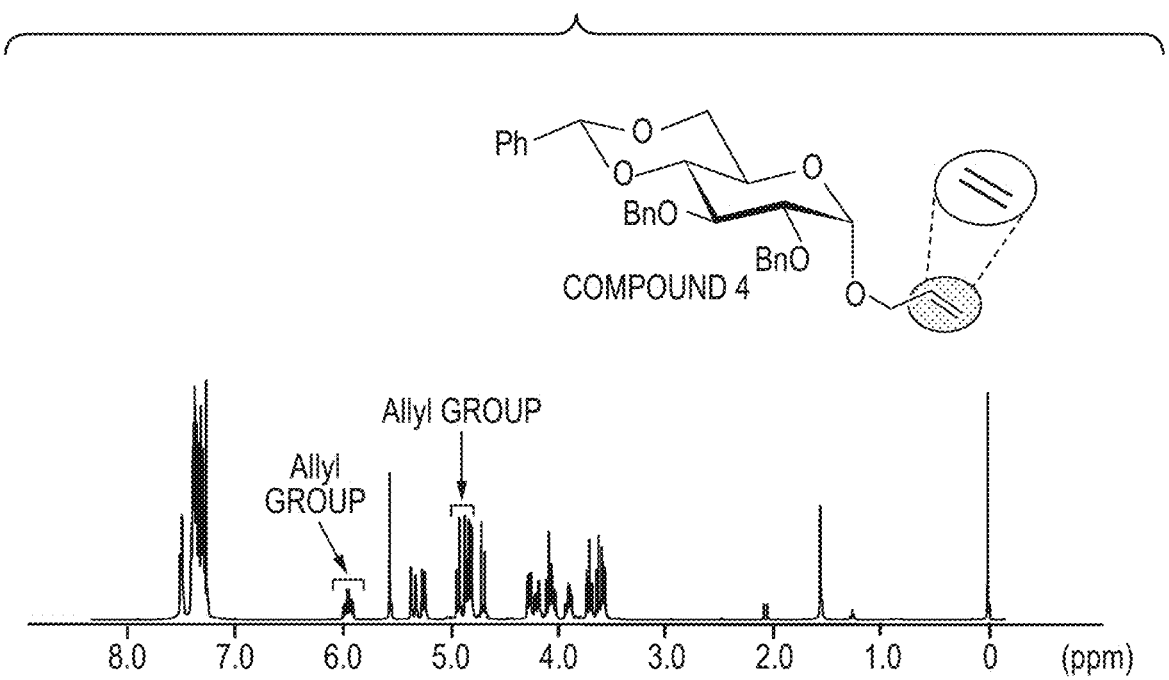
FIG. 6 is a diagram showing a result of $^1$H-NMR measurement of the compound represented by structural formula (5).
Figure 6:
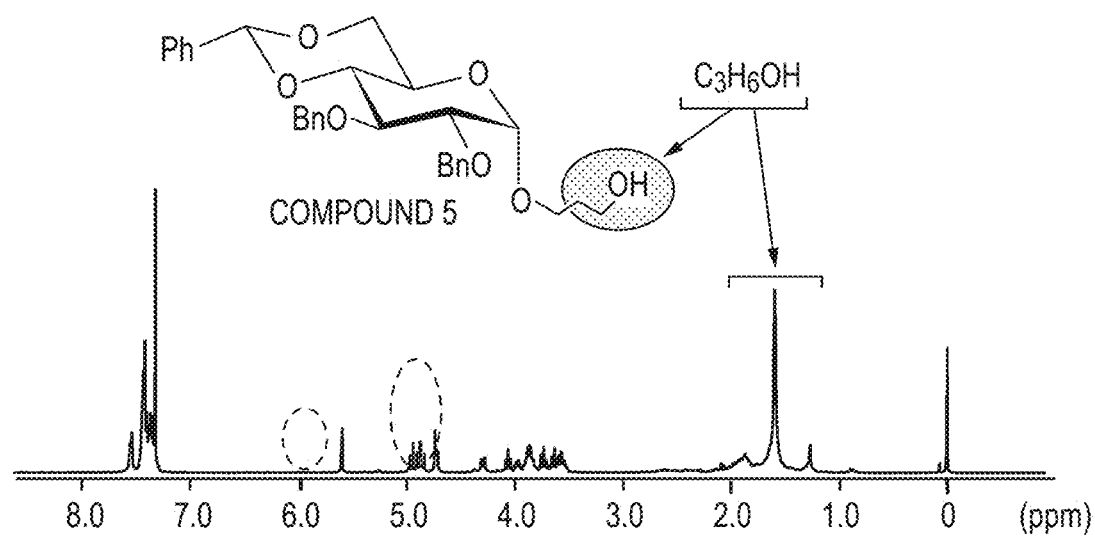

Mass spectrometry and a $^1$H-NMR spectrum of the compound represented by structural formula (5) are shown in FIGS. 5 and 6.

Data of the mass spectrometry and the $^1$H-NMR spectrum of the compound represented by structural formula (5) is shown below.

MS: measurement value m/z 529.28 [M+Na], calculation value 506.68 [M]

δ: 7.6-7.2 (15H), 6.0-3.5 (16H), 2.0-1.8 (2H)

In the pathway E, 3-(n-octadecyloxy)-n-propyl-2,3-di-O-benzyl-4,6-O-benzylidene-α-D-glucopyranoside (structural formula (6)) was synthesized. The compound (1.0 g) represented by structural formula (5) was dissolved in N,N-dimethylformamide (10 mL), 60% NaH (0.3 g) was added while the solution was stirred at 0° C., and thereafter the solution was stirred at the room temperature for 15 minutes. Then, stearyl bromide (1.3 g) was added, and the solution was stirred at the room temperature for 6 hours. 60% NaH (0.3 g) was again added, and the solution was stirred at 40° C. for 1 hour. Thereafter, the solution was brought back to the room temperature, methanol (5 mL) was added to stop reaction, and vacuum concentration was performed. The resultant residue suspended in a small amount of ethyl acetate was poured into water (20 mL), and extraction was performed with dichloromethane (10 mL, three times). After the residue was extracted and an organic phase was washed with Milli-Q water and a saturated saline solution, the organic phase was dried using sodium sulfate and filtered, and thereafter concentrated in a vacuum. The resultant residue was purified using silica gel chromatography (mixed solution of toluene and ethyl acetate) to obtain the compound represented by structural formula (6) (1.0 g, 99.0%) as a colorless oily substance.

Figure 7:
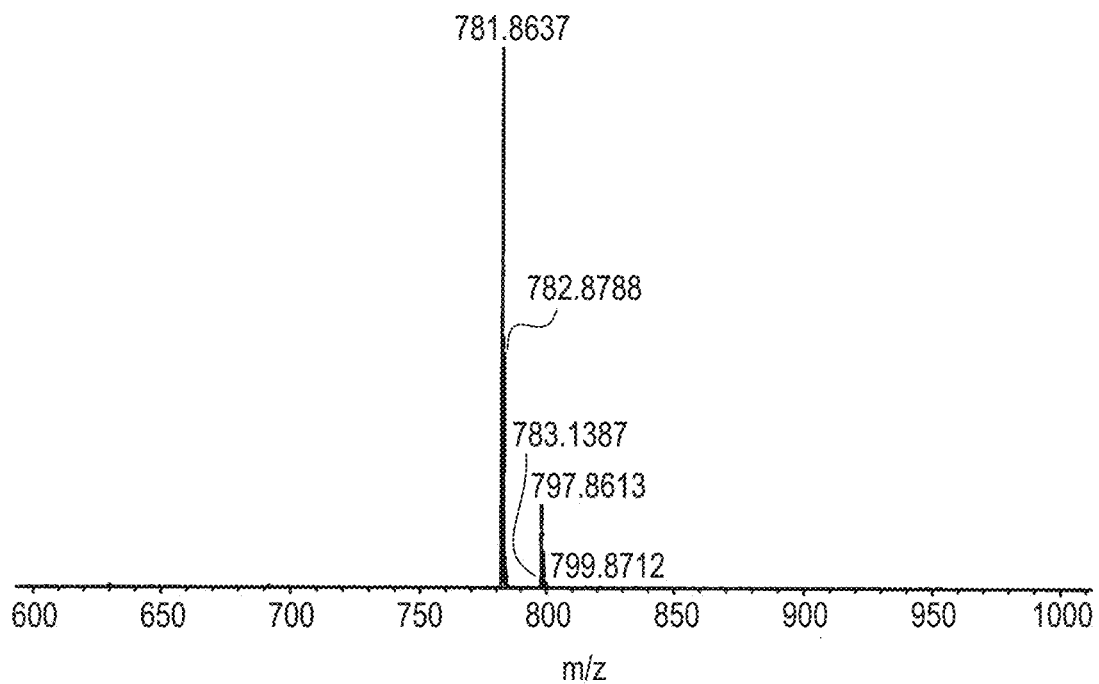
FIG. 7 is a diagram showing a result of mass spectrometry of a compound represented by structural formula (6).
Figure 8:
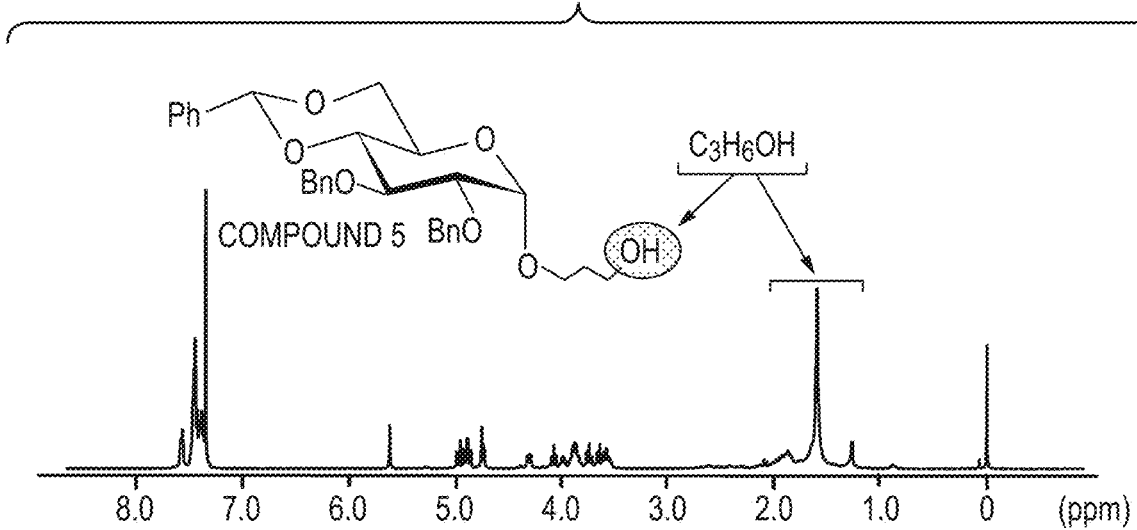
FIG. 8 is a diagram showing a result of $^1$H-NMR measurement of the compound represented by structural formula (6).
Figure 8:
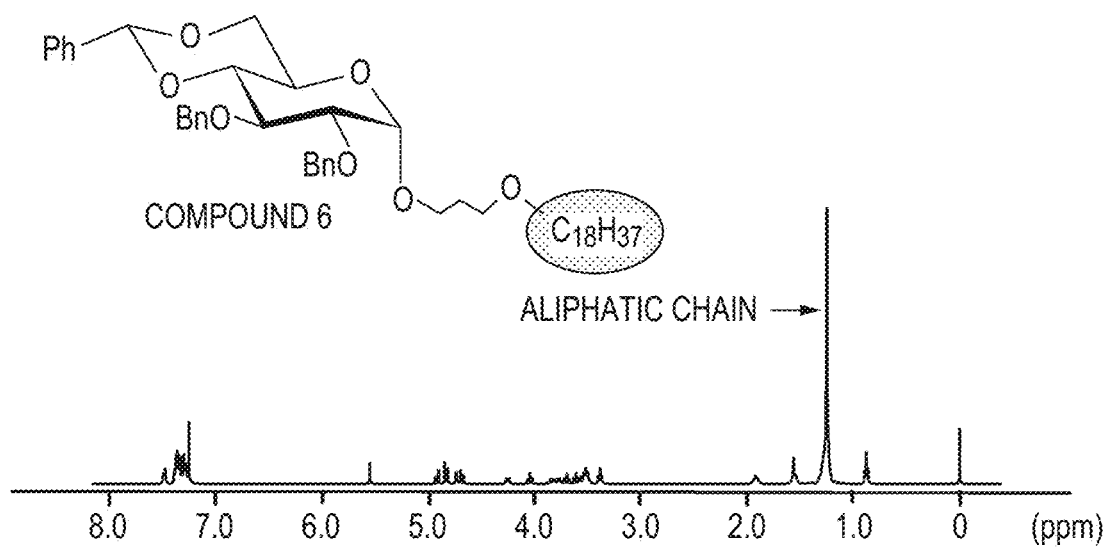

Mass spectrometry and a $^1$H-NMR spectrum of the compound represented by structural formula (6) are shown in FIGS. 7 and 8.

Data of the mass spectrometry and the $^1$H-NMR spectrum of the compound represented by structural formula (6) is shown below.

MS: measurement value m/z 781.86 [M+Na], calculation value 759.08 [M]

δ: 7.6-7.3 (15H), 5.7-3.3 (16H), 2.0-9.8 (39H)

In the pathway F, 3-(n-octadecyloxy)-n-propyl-2,3,4-tri-O-benzyl-α-D-glucopyranoside (structural formula (7)) was synthesized. The compound (0.5 g) represented by structural formula (6) was dissolved in dichloromethane (6.6 mL), and a tetrahydrofuran-borane tetrahydrofuran solution and trimethylsilyl triflate (17.9 μL) were added in a state where the solution was cooled with ice. The solution was stirred at the room temperature for 3 hours, and after the progress of reaction was confirmed, the solution was neutralized by adding triethylamine. Then, water (10 mL) was added, and extraction was performed with chloroform (100 mL, two times). An organic phase was washed with a 1 M HCl solution, sodium bicarbonate water, and a saturated saline solution, in this order. Thereafter, the organic phase was dried using sodium sulfate and filtered, and then concentrated in a vacuum. The resultant residue was purified using silica gel chromatography (mixed solution of toluene and ethyl acetate) to obtain the compound represented by structural formula (7) (0.43 g, 85.3%).

Figure 9:
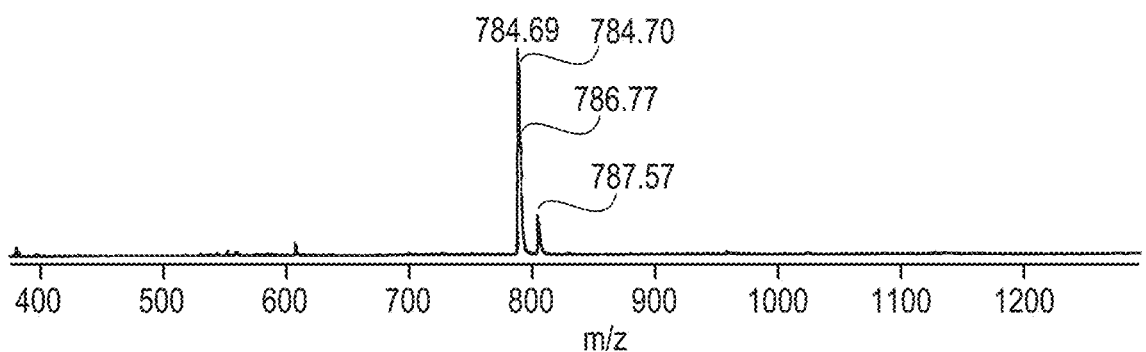
FIG. 9 is a diagram showing a result of mass spectrometry of a compound represented by structural formula (7).
Figure 10:
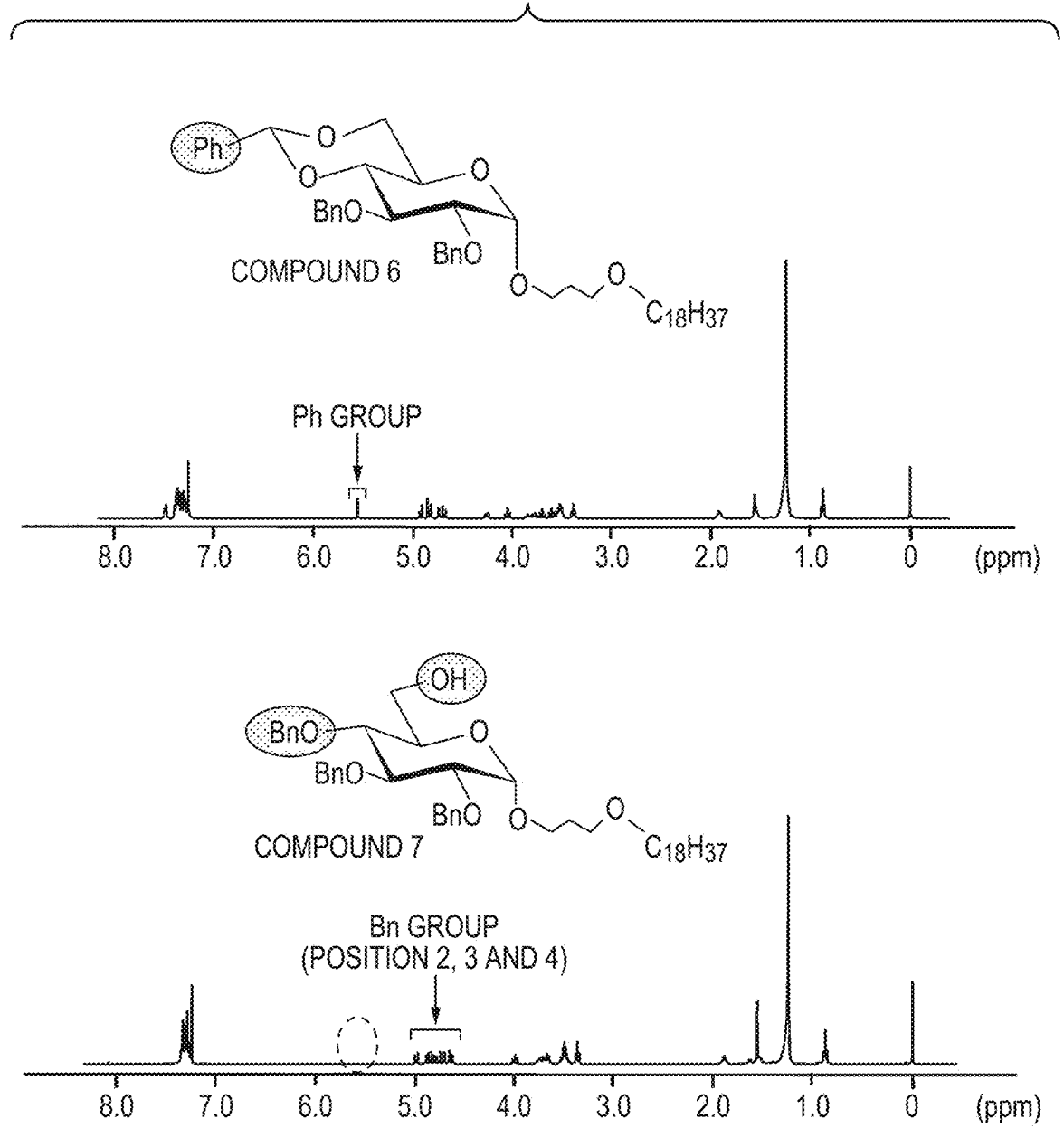
FIG. 10 is a diagram showing a result of $^1$H-NMR measurement of the compound represented by structural formula (7).

Mass spectrometry and a $^1$H-NMR spectrum of the compound represented by structural formula (7) are shown in FIGS. 9 and 10.

Data of the mass spectrometry and the $^1$H-NMR spectrum of the compound represented by structural formula (7) is shown below.

MS: measurement value m/z 784.69 [M+Na], calculation value 761.10 [M]

δ: 7.6-7.3 (15H), 5.1-4.6 (17H), 2.0-9.8 (39H)

In the pathway G, 3-(n-octadecyloxy)-n-propyl-2,3,4-tri-O-benzyl-6-O-tosyl-α-D-glucopyranoside (structural formula (8)) was synthesized. p-toluenesulfonyl chloride (0.07 g) was added to a pyridine solution (0.50 mL) of the compound (0.10 g) represented by structural formula (7) in a state where the solution was cooled to 0° C. with ice water in an argon atmosphere, and then the solution was brought back to the room temperature and stirred for 4 hours. After it was confirmed through thin layer chromatography (TLC) that reaction had ended, the solution was cooled to 0° C. with ice water and neutralized by adding methanol. Thereafter, the residue suspended in a small amount of ethyl acetate was poured into 1 M hydrochloric acid (1 mL) and was extracted with ethyl acetate (2 mL, three times). A collected organic phase was washed with a saturated saline solution (1 mL, two times), a saturated sodium hydrogen carbonate solution (1 mL, two times), and a saturated saline solution (1 mL, two times), in this order, and was dried using sodium sulfate and filtered, and then concentrated in a vacuum. The concentrate (0.146 g) was dissolved in chloroform and purified using silica gel chromatography (mixed solution of toluene and ethyl acetate) to obtain the compound represented by structural formula (8) (0.08 g, 95.3%).

Figure 11:
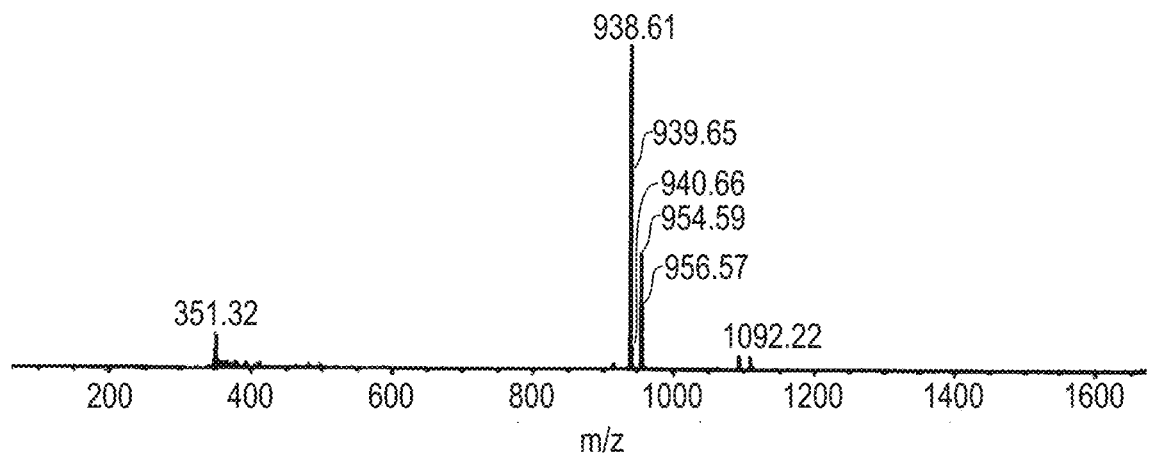
FIG. 11 is a diagram showing a result of mass spectrometry of a compound represented by structural formula (8).
Figure 12:
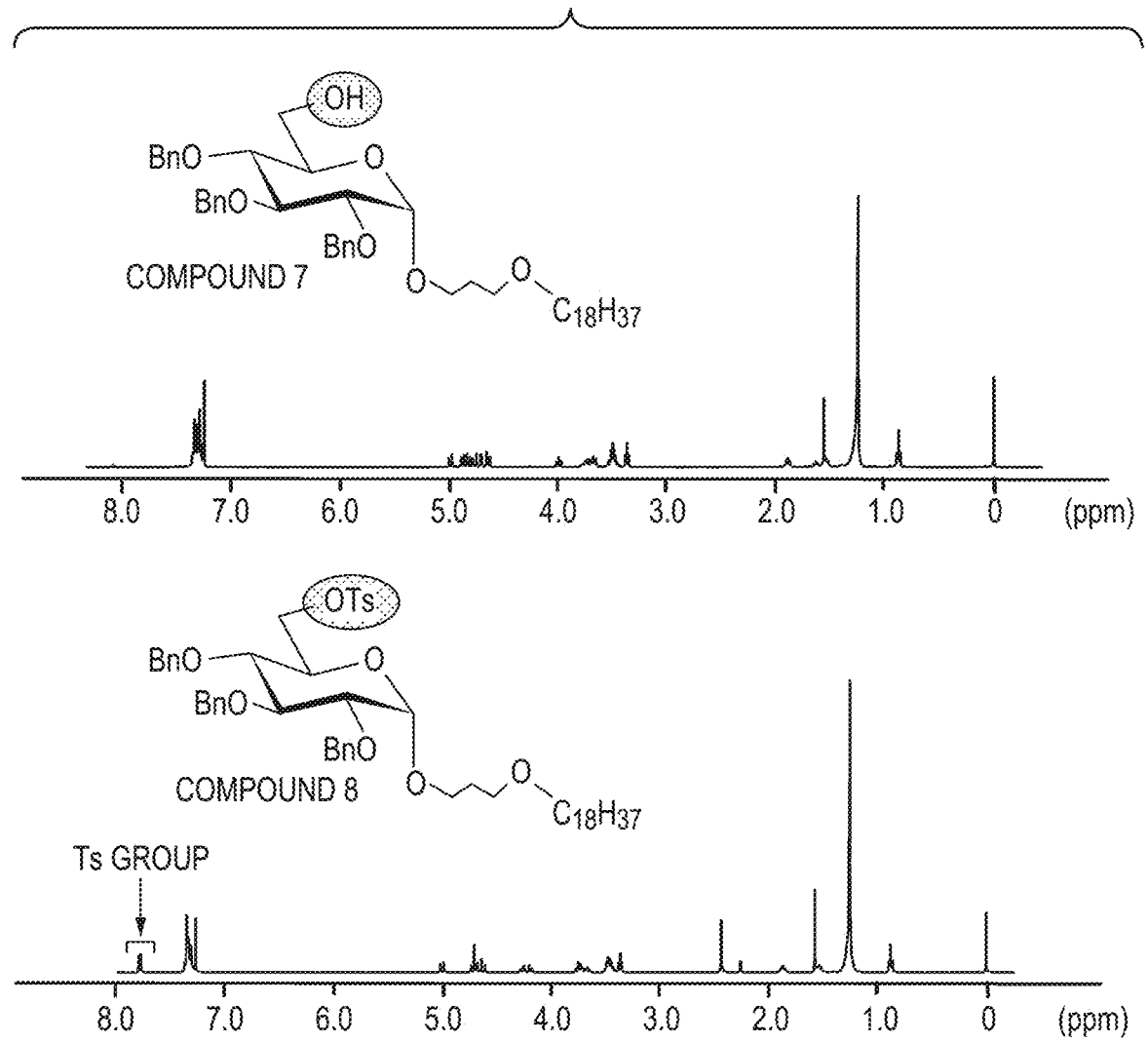
FIG. 12 is a diagram showing a result of $^1$H-NMR measurement of the compound represented by structural formula (8).

Mass spectrometry and a $^1$H-NMR spectrum of the compound represented by structural formula (8) are shown in FIGS. 11 and 12.

Data of the mass spectrometry and the $^1$H-NMR spectrum of the compound represented by structural formula (8) is shown below.

MS: measurement value m/z 938.61 [M+Na], calculation value 915.28 [M]

δ: 7.8-7.2 (19H), 5.1-3.3 (11H), 2.5-0.8 (42H)

In the pathway H, 3-(n-octadecyloxy)-n-propyl-2,3,4-tri-O-benzyl-6-thioacetyl-α-D-glucopyranoside (structural formula (9)) was synthesized. Anhydrous ethanol (1 mL) and potassium thioacetate (0.02 g) were added to the compound (0.05 g) represented by structural formula (8) in an argon atmosphere, and the mixture was stirred at 80° C. for 4 hours. After the progress of reaction was confirmed, cold water (1 mL) was poured in a state where the mixture was cooled with ice, and extraction was performed with ethyl acetate (3 mL, two times). Next, a collected organic phase was washed with a 1 M sodium hydroxide aqueous solution (1 mL, two times) and a saturated saline solution (1 mL, two times), in this order, and was dried using sodium sulfate and filtered, and then concentrated in a vacuum. The obtained residue was purified using silica gel chromatography (mixed solution of hexane and ethyl acetate) to obtain the compound represented by structural formula (9) (0.43 g, 85.3%) as a light brown oily substance.

Figure 13:
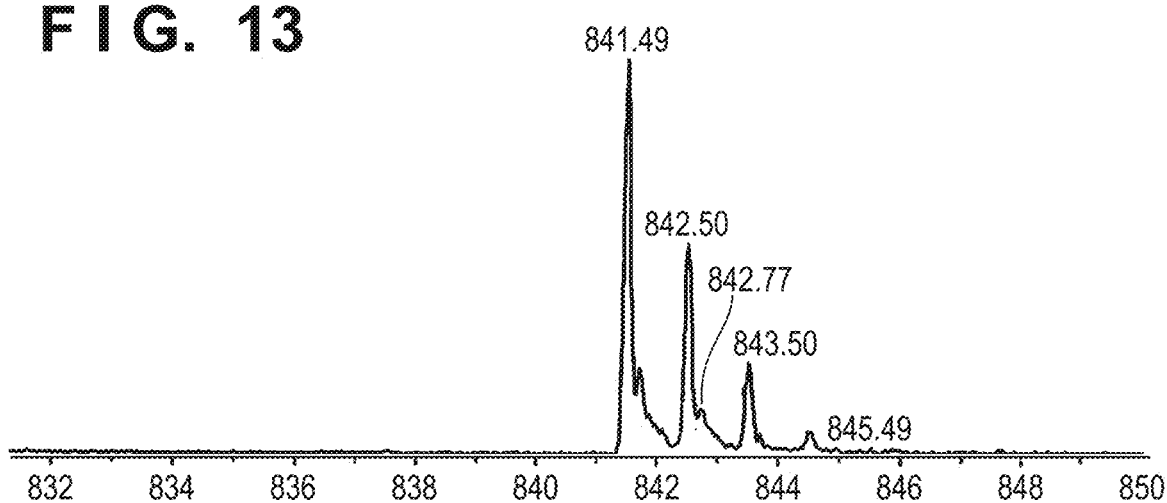
FIG. 13 is a diagram showing a result of mass spectrometry of a compound represented by structural formula (9).
Figure 14:
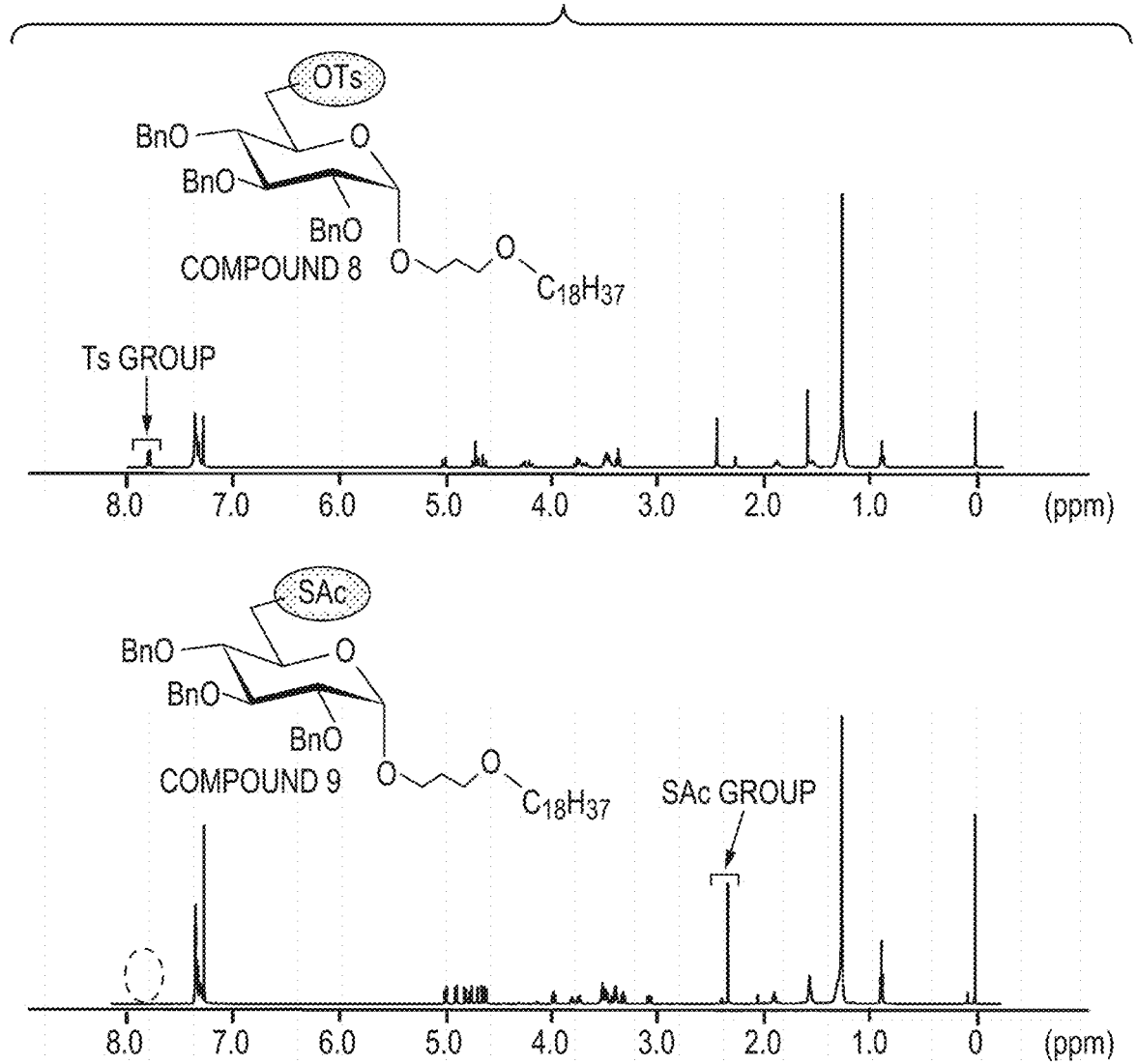
FIG. 14 is a diagram showing a result of $^1$H-NMR measurement of the compound represented by structural formula (9).

Mass spectrometry and a $^1$H-NMR spectrum of the compound represented by structural formula (9) are shown in FIGS. 13 and 14.

Data of the mass spectrometry and the $^1$H-NMR spectrum of the compound represented by structural formula (9) is shown below.

MS: measurement value m/z 841.49 [M+Na], calculation value 819.20[M]

δ: 7.4-7.2 (15H), 5.0-3.1 (17H), 2.5-0.8 (42H)

In the pathway I, 3-(n-octadecyloxy)-n-propyl-2,3,4-tri-O-benzyl-α-D-quinovopyranoside sodium salt (structural formula (10)) was synthesized. Glacial acetic acid (3.4 mL), potassium acetate (0.35 g), and OXONE (0.13 g) were added in this order to the compound (0.05 g) represented by structural formula (9), and the mixture was vigorously stirred at the room temperature for 4 hours. After it was confirmed that reaction had sufficiently progressed, the reaction liquid was poured into cold water (5.4 mL) and stirred. Next, extraction was performed with ethyl acetate (2 mL, two times), and a collected organic phase was washed with a saturated sodium hydrogen carbonate solution (2 mL, two times) and a saturated saline solution (2 mL, two times), in this order, and was dried using sodium sulfate and filtered, and then concentrated in a vacuum. The resultant residue was purified using silica gel chromatography (mixed solution of dichloromethane and methanol) to obtain the compound represented by structural formula (10) (0.01 g, 37.6%) as a colorless wax-like substance.

Figure 15:
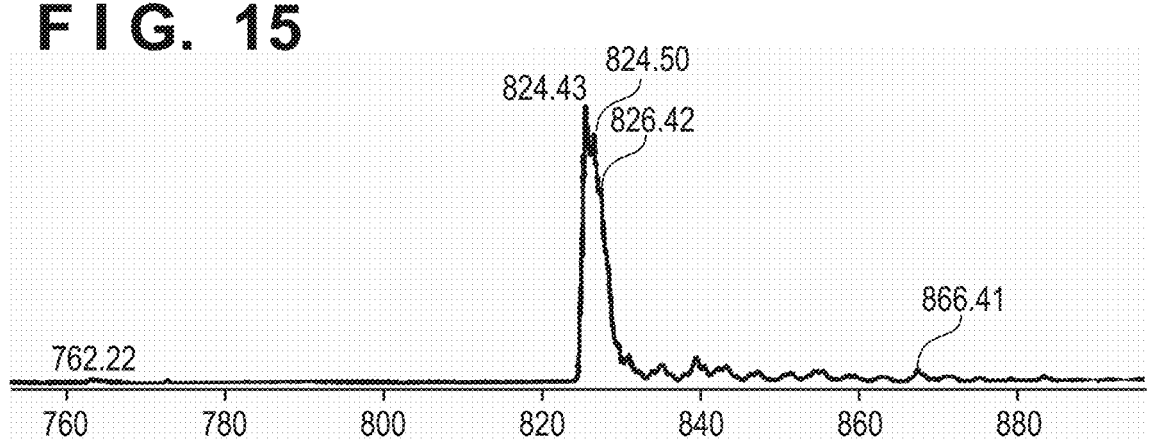
FIG. 15 is a diagram showing a result of mass spectrometry of a compound represented by structural formula (10).
Figure 16:
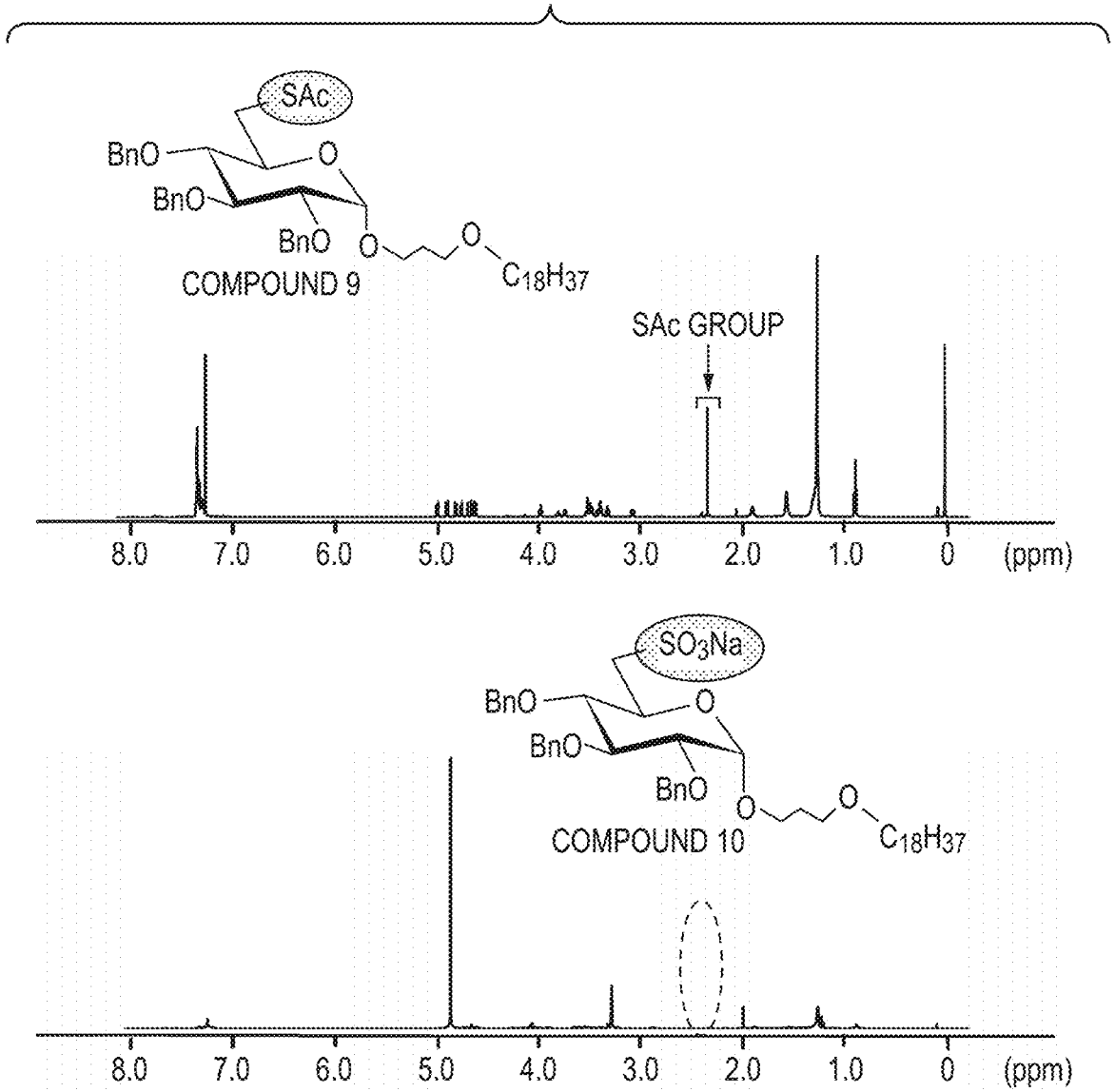
FIG. 16 is a diagram showing a result of $^1$H-NMR measurement of the compound represented by structural formula (10).

Mass spectrometry and a $^1$H-NMR spectrum of the compound represented by structural formula (10) are shown in FIGS. 15 and 16.

Data of the mass spectrometry and the $^1$H-NMR spectrum of the compound represented by structural formula (10) is shown below.

MS: measurement value m/z 824.43[M-Na], calculation value 847.14[M]

δ: 7.4-7.2 (15H), 5.0-3.1 (17H), 2.5-0.8 (39H)

In the pathway J, 3-(n-octadecyloxy)-n-propyl-α-D-quinovopyranoside sodium salt (structural formula (11)) was synthesized. The compound (0.007 g) represented by structural formula (10) was dissolved in ethanol (1.6 mL), palladium carbon (0.032 g) was added, and the mixture was stirred at 30° C. for 16 hours in a hydrogen gas atmosphere. After it was confirmed that reaction had sufficiently progressed, palladium activated carbon was filtered, and the filtrate was concentrated in a vacuum. After methanol (2 mL) and toluene (2 mL) were added to the obtained residue and the solution was vigorously stirred, the solvents were distilled under reduced pressure to obtain a colorless liquid mixture. The concentrated residue was purified using silica gel chromatography (mixed solution of chloroform and methanol) to obtain the compound represented by structural formula (11) (0.004 g, 81.6%).

Figure 17:
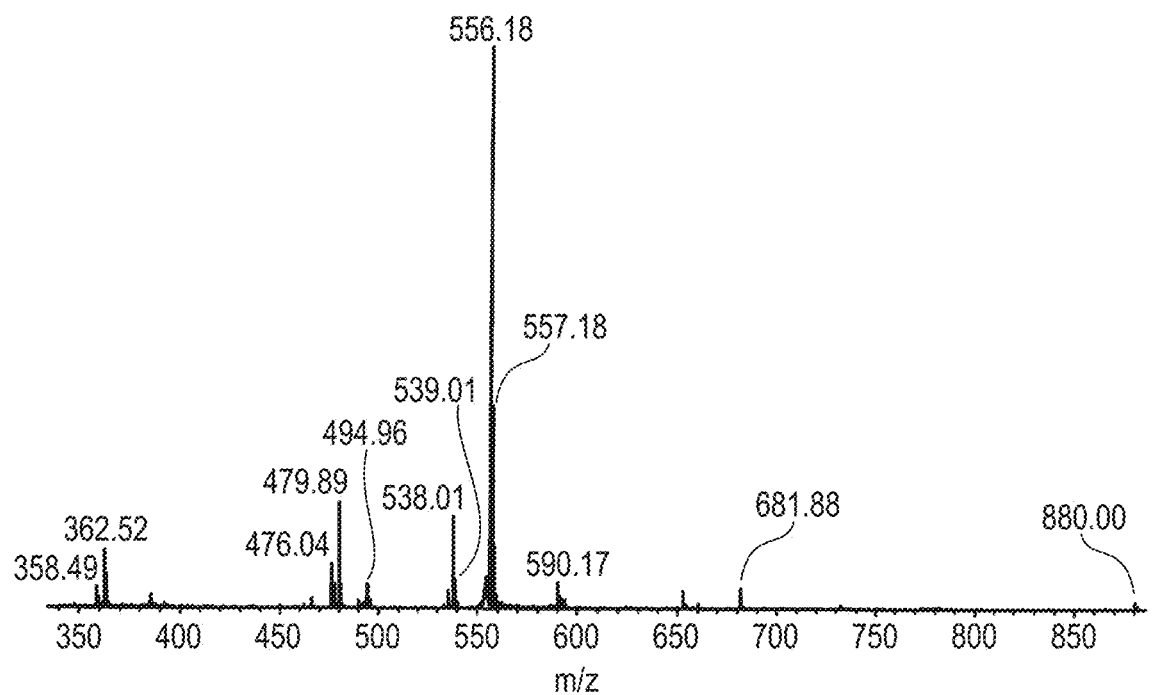
FIG. 17 is a diagram showing a result of mass spectrometry of a compound represented by structural formula (11).
Figure 18:
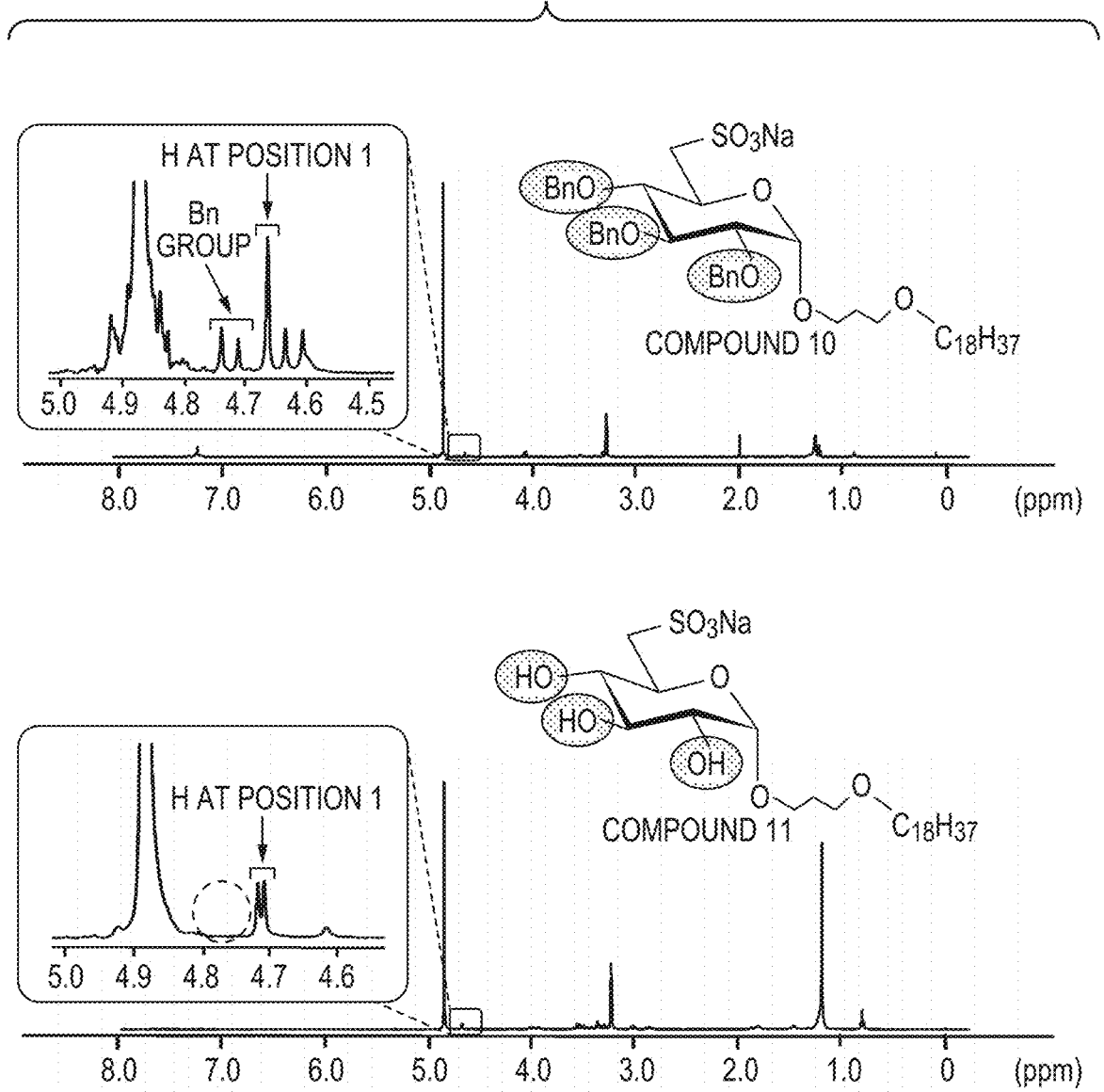
FIG. 18 is a diagram showing a result of $^1$H-NMR measurement of the compound represented by structural formula (11).

Mass spectrometry and a $^1$H-NMR spectrum of the compound represented by structural formula (11) are shown in FIGS. 17 and 18.

Data of the mass spectrometry and the $^1$H-NMR spectrum of the compound represented by structural formula (11) is shown below.

MS: measurement value m/z 556.16 [M+Na], calculation value 576.33[M]

δ: 5.0-2.8 (17H), 4.8-2.8 (11H), 1.0-0.8 (37H) Test as candidate compound for radiosensitizer In the following, the compound (compound (A)) represented by structural formula (11) and a sulfopyranosylacyl propanediol derivative (compound (B)) that is described in Patent Document 2 and is used as a radiosensitizer were used as test compounds, and test results of these compounds are shown for respective tests in FIGS. 19 and 20.

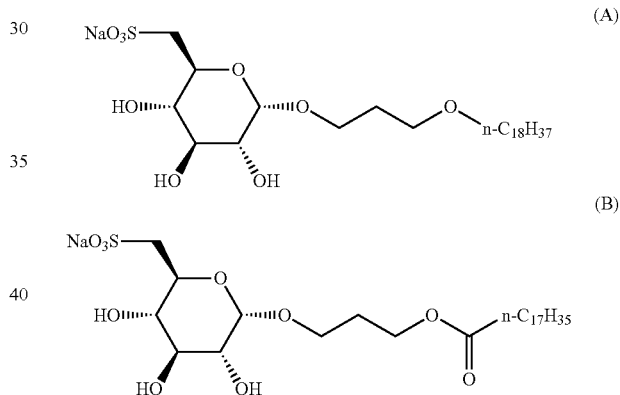

Fetal bovine serum (FBS) (manufactured by Sigma-Aldrich) was added to RPMI1640 (manufactured by Sigma-Aldrich) such that a final concentration was 10%. Further, penicillin G potassium (manufactured by Meiji Seika) and Streptomycin (manufactured by Meiji Seika) were each added in an amount of 0.1 mg/mL, and the thus obtained solution was used as a culture medium in the following test. Also, a CellROX Green Reagent solution (manufactured by Thermo Fisher Scientific) was used as a reagent.

Adenocarcinomic human alveolar basal epithelial cell line A549 cells were suspended in the RPMI1640 medium (1.0×10^5 cells/mL), and the suspension was poured into a 96-well plate in an amount of 100 μL for each well. Thereafter, the cells were cultivated under a 5% $CO_2$ moisture-saturated condition at 37° C. so as to attach to the plate, and after the cultivation was performed for 24 hours, the medium was removed by suction and the cells were washed with PBS. Next, 100 μL of PBS and 100 μL of a suspension of the test compound suspended in PBS (containing 10% PBS) were separately added. After the medium was cultivated under a 5% $CO_2$ moisture-saturated condition at 37° C. for 1 hour, the CellROX Green Reagent solution was added to each well such that a final concentration was 5 μL, and the medium was again cultivated under a 5% $CO_2$ moisture-saturated condition at 37° C. for 30 minutes. After the cultivation was performed for 30 minutes, washing was performed using PBS, and fluorescence intensity at an excitation wavelength of 485 nm and a detection wavelength of 520 nm was measured. An ROS production ratio of each test compound was calculated by taking the value of fluorescence intensity of a well to which only PBS that did not contain the test compound was added to be 1.

Figure 19:
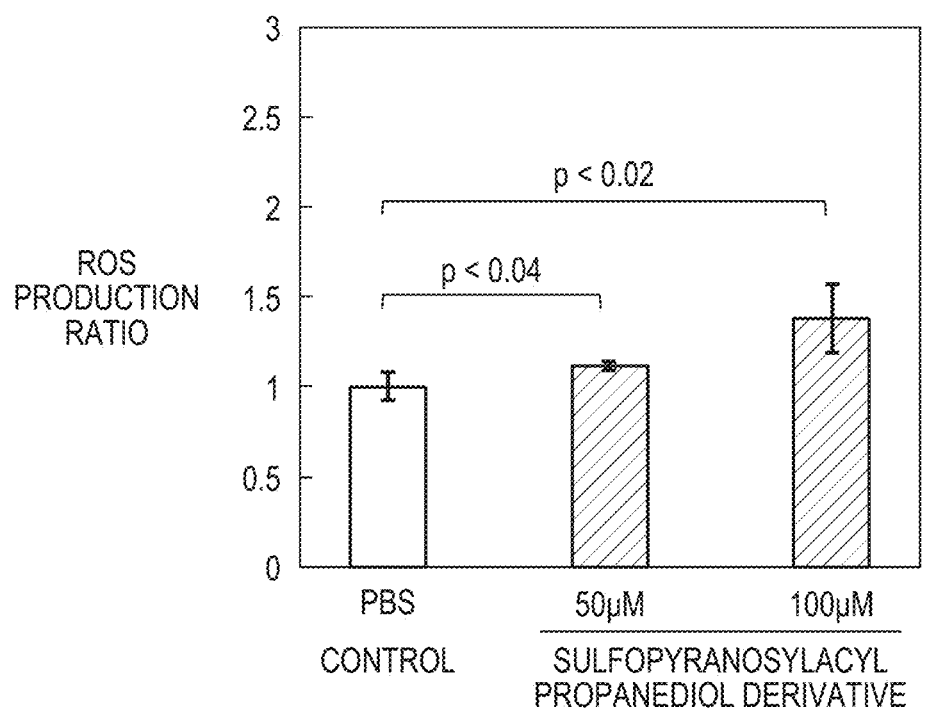
FIG. 19 is a diagram showing a result of experiment of a radiosensitizing effect.
Figure 19:
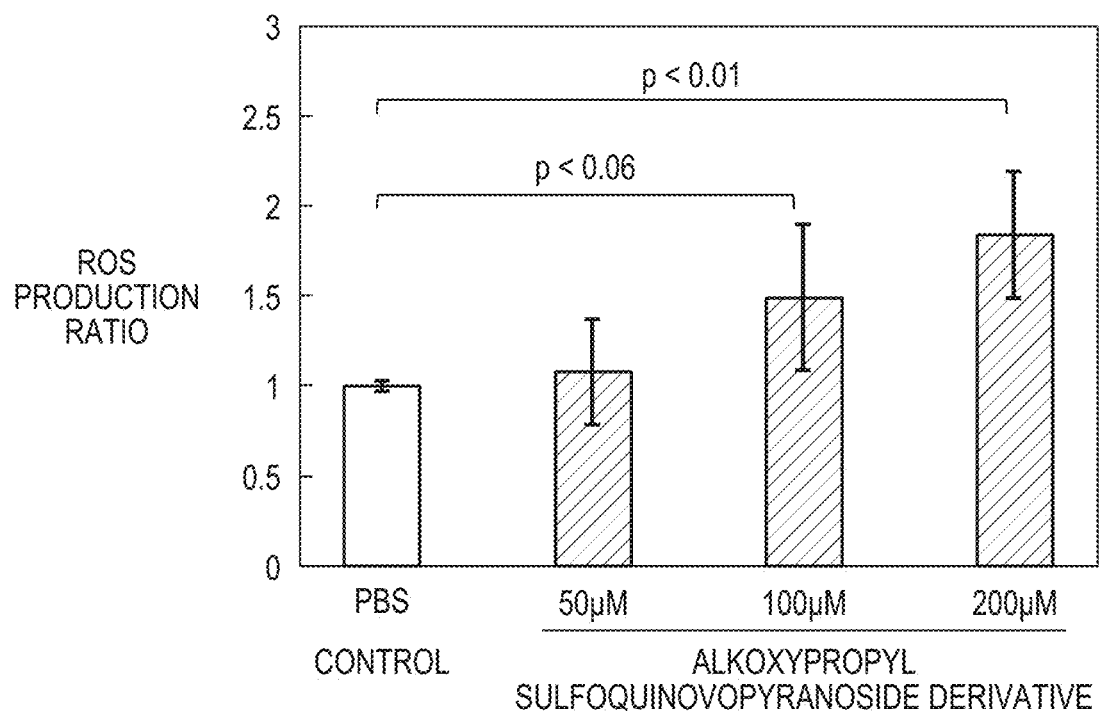

The calculated ROS production ratios are shown in FIG. 19. It was confirmed that the compound (A) induced production of the ROS in the adenocarcinomic human alveolar basal epithelial cell line A549 cells, similarly to the sulfopyranosylacyl propanediol derivative such as the compound (B). Therefore, the compound represented by general formula (I) according to the present invention and pharmaceutically acceptable salts thereof can be used as a radiosensitizer or a reagent for emitting reactive oxygen in a living body.

Hydrolysis Resistance Test

The test compound and lipase for organic synthesis (Lipase PS Amano SD, manufactured by FUJIFILM Wako Pure Chemical Corporation) were each adjusted using PBS so as to have a concentration of 1.3 μg/μL. Next, the thus obtained reaction solution was developed by TLC using an eluent (chloroform:methanol=1:1) and was analyzed. A sample that was taken before reaction progressed, a sample that was taken when 2 hours elapsed, and a sample that was taken when 4 hours elapsed were each used as the reaction solution to be developed. As for the reaction solution in which the compound (A) was used as the test compound, analysis was also performed on a sample that was taken when 18 hours elapsed from the start of reaction. TLC aluminum sheet silica gel 60 F254 (manufactured by Merck) was used as the TLC.

Figure 20:
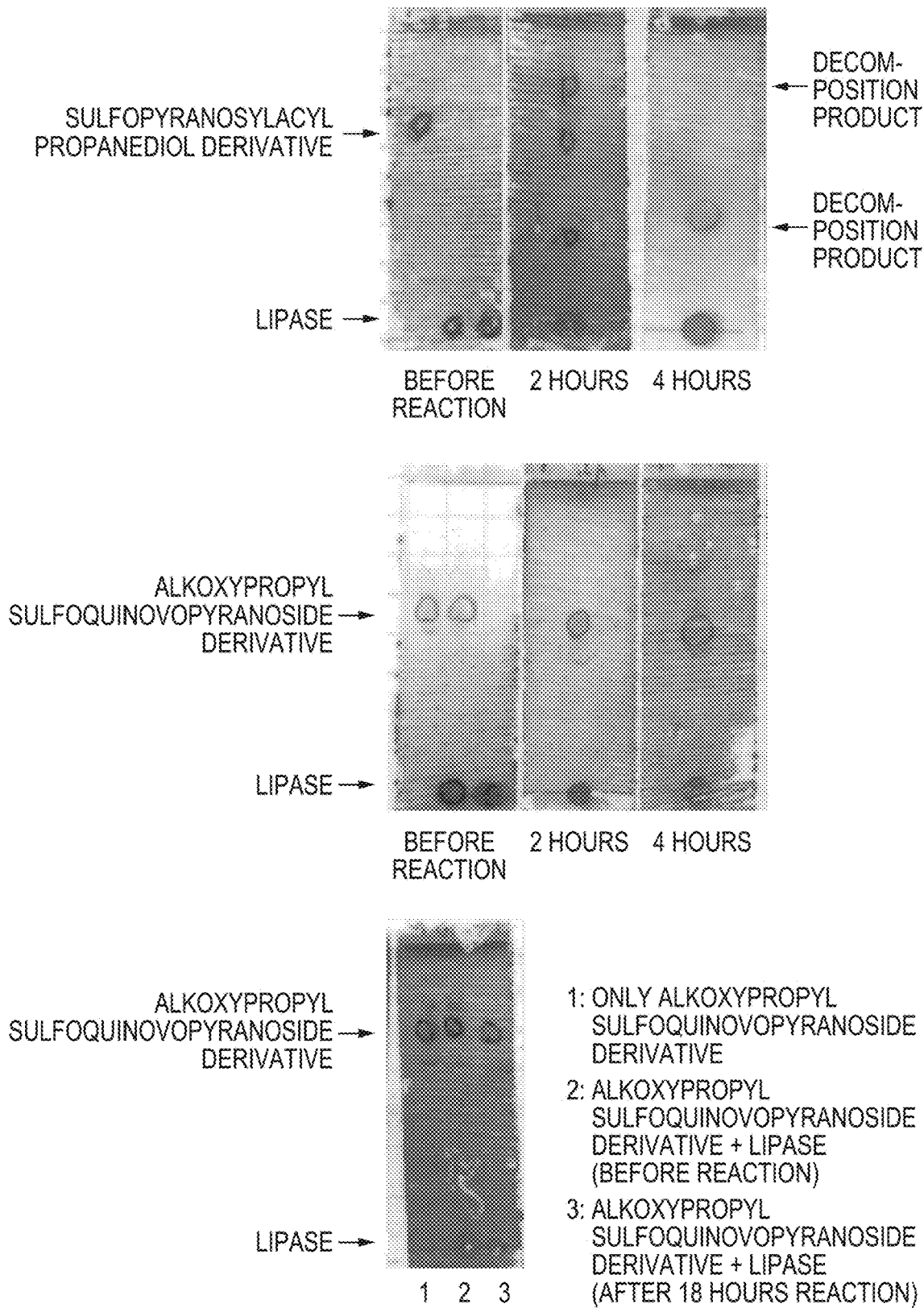
FIG. 20 is a diagram showing a result of experiment of resistance to hydrolysis.

Analysis results are shown in FIG. 20. It was confirmed that in the case where the sulfopyranosylacyl propanediol derivative such as the compound (B) was used as the test compound, the test compound was completely decomposed when 4 hours elapsed from the start of reaction. On the other hand, it was confirmed that in the case where the compound (A) was used as the test compound, the test compound was not completely decomposed even when 18 hours elapsed from the start of reaction. This result shows that the compound (A) has more excellent resistance to hydrolysis than the sulfopyranosylacyl propanediol derivative.

Therefore, it was shown that the compound represented by general formula (I) according to the present invention and pharmaceutically acceptable salts thereof are stable against lipase and continuously exhibit effectiveness as a sensitizer in cancer tissue for a longer period of time than the sulfopyranosylacyl propanediol derivative.

The invention is not limited to the foregoing embodiments, and various variations/changes are possible within the spirit of the invention.

What is claimed is:

1. A compound represented by the following formula (I) or a salt thereof,

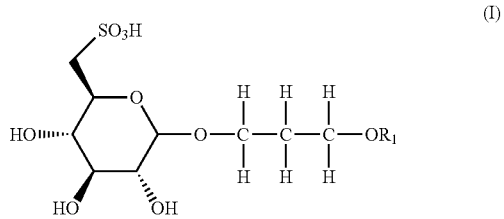

(I)

wherein $R_1$ is an aliphatic hydrocarbon group having 10 to 26 carbon atoms.

2. The compound according to claim 1 or a salt thereof, wherein $R_1$ is an octadecyl group.

* * * * *